United States Patent
Halderman et al.

(10) Patent No.: US 6,597,444 B1
(45) Date of Patent: *Jul. 22, 2003

(54) DETERMINATION OF FLUX COVERAGE

(75) Inventors: Jonathan D. Halderman, San Jose, CA (US); Terri J. Brownfield, Boulder Creek, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/627,436

(22) Filed: Jul. 28, 2000

Related U.S. Application Data

(60) Provisional application No. 60/214,855, filed on Jun. 28, 2000.

(51) Int. Cl.[7] .................. G01N 21/00; H01L 21/66
(52) U.S. Cl. .................. 356/237.1; 356/630; 438/5; 438/7; 438/16; 228/180.22
(58) Field of Search .................. 356/630, 631, 356/632, 237.1, 237.2, 237.3, 237.4; 438/15, 5, 7, 14, 16; 228/102, 35, 214, 223

(56) References Cited

U.S. PATENT DOCUMENTS

| | | | |
|---|---|---|---|
| 4,276,186 A | | 6/1981 | Bakos et al. .................. 252/158 |
| 4,752,027 A | * | 6/1988 | Gschwend ............... 228/180.2 |
| 5,120,966 A | * | 6/1992 | Kondo ..................... 250/372 |
| 5,415,337 A | * | 5/1995 | Hogan et al. ............... 228/223 |
| 5,922,606 A | | 7/1999 | Jenkins et al. ............... 436/55 |
| 5,932,021 A | | 8/1999 | Cala et al. ..................... 134/2 |
| 5,988,485 A | | 11/1999 | Master et al. ............ 228/180.22 |
| 6,038,525 A | * | 3/2000 | Maguire et al. ............. 702/172 |
| 6,039,805 A | | 3/2000 | Davis et al. ................. 118/74 |
| 6,059,894 A | | 5/2000 | Pendse ....................... 148/23 |
| 6,098,867 A | * | 8/2000 | Master et al. ............... 228/102 |
| 6,258,612 B1 | * | 7/2001 | Master et al. ................. 438/15 |

FOREIGN PATENT DOCUMENTS

| | | | |
|---|---|---|---|
| JP | 8-250846 | * | 9/1996 |

* cited by examiner

Primary Examiner—Hoa Q. Pham

(57) ABSTRACT

A package assembly is formed by applying flux to a substrate and inspecting the applied flux to determine whether the amount applied is adequate to form reliable interconnections between a device and the substrate. Embodiments include applying a rosin based flux on a laminate substrate and inspecting the coverage of the applied flux by fluorescent spectroscopy.

13 Claims, 2 Drawing Sheets

DETERMINATION OF FLUX COVERAGE

RELATED APPLICATION

This application claims priority from U.S. Provisional Application Serial No. 60/214,855 filed Jun. 28, 2000 entitled "Determination of Flux Coverage" which is incorporated in its entirety herein by reference hereby.

FIELD OF THE INVENTION

The present invention relates generally to semiconductor packaging technology and the manufacture of package assemblies. The present invention has particular applicability to methods of inspecting flux that has been applied to a substrate during assembly of a device package.

BACKGROUND

Integrated circuit devices are typically electronically packaged by mounting one or more integrated circuit (IC) chips or dies to a substrate, sometimes referred to as a carrier. In a flip chip assembly or package, the die is "bumped" with solder to form a plurality of discrete solder balls over metal contacts on the surface of the die. The chip is then turned upside down or "flipped" so that the device side or face of the IC die can be mounted to a substrate having a corresponding array of metal contacts. Typically, the metal contacts of the substrate are coated or formed with a solder alloy. Electrical interconnection of the die to the substrate is conventionally performed by aligning the die to the substrate and reflowing the solder on the die and/or the substrate to electrically and mechanically join the parts. Directly coupling the die immediately below the substrate allows for an increased number of interconnections and improves voltage noise margins and signal speed.

Typically, a flux composition is applied to either the die or the substrate to facilitate the formation of the interconnect. Flux acts as an adhesive to hold the placed components in place pending soldering and further acts to minimize metallic oxidation that occurs at soldering temperatures thereby improving the electrical and mechanical interconnection and reliability between the soldered component and substrate. Soldering fluxes fall into three broad categories: rosin fluxes, water-soluble fluxes, and no-clean fluxes. Rosin fluxes, which have a relatively long history of use, are still widely used in the electronics industry. Water-soluble fluxes, which are a more recent development and which are increasingly used in consumer electronics, are highly corrosive materials. No-clean fluxes, a very recent development, reportedly do not require removal from the circuit assemblies. The most common flux for IC die attach packaging comprises a suspension liquid of various acids suspended in an alcohol base.

It has been observed that controlling the amount of applied flux is important irrespective of the type of flux employed in a particular packaging process, since enough flux must be used to effect a reliable metallurgical bond to electrically and mechanically interconnect the component to the substrate. Too much applied flux, however, can undesirably cause displacement of the placed component due to flux boiling. Excess flux further adversely impacts other circuit board manufacturing processes. For example, traces of the soldering flux residues which remain after solder reflow can lead to circuit failure, delamination of underfill, etc.

Accordingly, a continual need exists for improved processes and/or assemblies for the packaging of electronic components on to substrates employing solder fluxes.

SUMMARY OF THE INVENTION

An advantage of the present invention is a high yield, high through-put process for inspecting the coverage and/or uniformity of applied flux during assembly of a device package.

Additional advantages and features of the invention will be set forth in part in the description which follows and in part will become apparent to those having ordinary skill in the art upon examination of the following or may be learned from the practice of the invention. The advantages of the invention may be realized and obtained as particularly pointed out in the appended claims.

According to the present invention, the foregoing and other advantages are achieved in part by a method of inspecting the application of flux on a substrate. The method comprises applying flux to the substrate over a preselected area, e.g. over an array of conductive contacts suitable for mounting a device to form a flux zone having an area. In an embodiment of the present invention, the flux is applied to cover approximately the same area occupied by an array of conductive contacts, e.g. an array of landing pads, on the substrate.

In practicing the invention, the flux zone area is inspected by optical or electro-optical spectroscopy. Embodiment of the present invention include applying a rosin flux to a chip area on a laminate substrate and inspecting the coverage and/or uniformity of the applied flux by fluorescence and/or infrared spectroscopy.

Another aspect of the present invention is a method of manufacturing an interconnected device assembly. The method comprises: providing a substrate having conductive contacts thereon for mounting a device, providing a device having a plurality, e.g. an array, of solder contacts thereon; applying a flux to the substrate to form a flux zone on the substrate; inspecting the flux zone area by optical or electro-optical spectroscopy; contacting the device and substrate such that the solder contacts of the device are aligned with the conductive contacts on the substrate to form a substrate/assembly; and forming an electrical connection between the solder contacts of the device and the conductive contacts on the substrate. The amount of flux that will be satisfactory depends on several factors, often requiring empirical determinations.

By monitoring the coverage of the applied flux prior to assembling the semiconductor device and substrate, the present invention advantageously provides an essentially instant and continuous method for determining adequate coverage and/or uniformity of the applied flux during the packaging process. In an embodiment of the present invention, the flux covering an area defined by the perimeter of the array of conductive contacts on the substrate is from about 50% to about 150%, e.g. approximately 100% of the area defined by the perimeter of the array of conductive contacts on the substrate.

Additional advantages of the present invention will become readily apparent to those skilled in this art from the following detailed description, wherein only the preferred embodiment of the present invention is shown and described, simply by way of illustration of the best mode contemplated for carrying out the present invention. As will be realized, the invention is capable of other and different embodiments, and its several details are capable of modifications in various obvious respects, all without departing from the present invention. Accordingly, the drawing and description are to be regarded as illustrative in nature, and not as restrictive.

DESCRIPTION OF THE INVENTION

The present invention addresses and solves the problem of random and systematic variations in the coverage and uniformity of flux applied to a substrate caused by variations in flux composition, fluctuations in process parameters, varied pattern densities, etc. by a non-contact inspection technique performed during assembly of a device and substrate. The present invention enables the manufacture of semiconductor packages, particularly flip chip package assemblies, with improved control over the fluxing process and with an attendant increase in device performance. The present invention advantageously enables in-situ process control and closed-loop control over the fluxing procedure.

Figure 1:
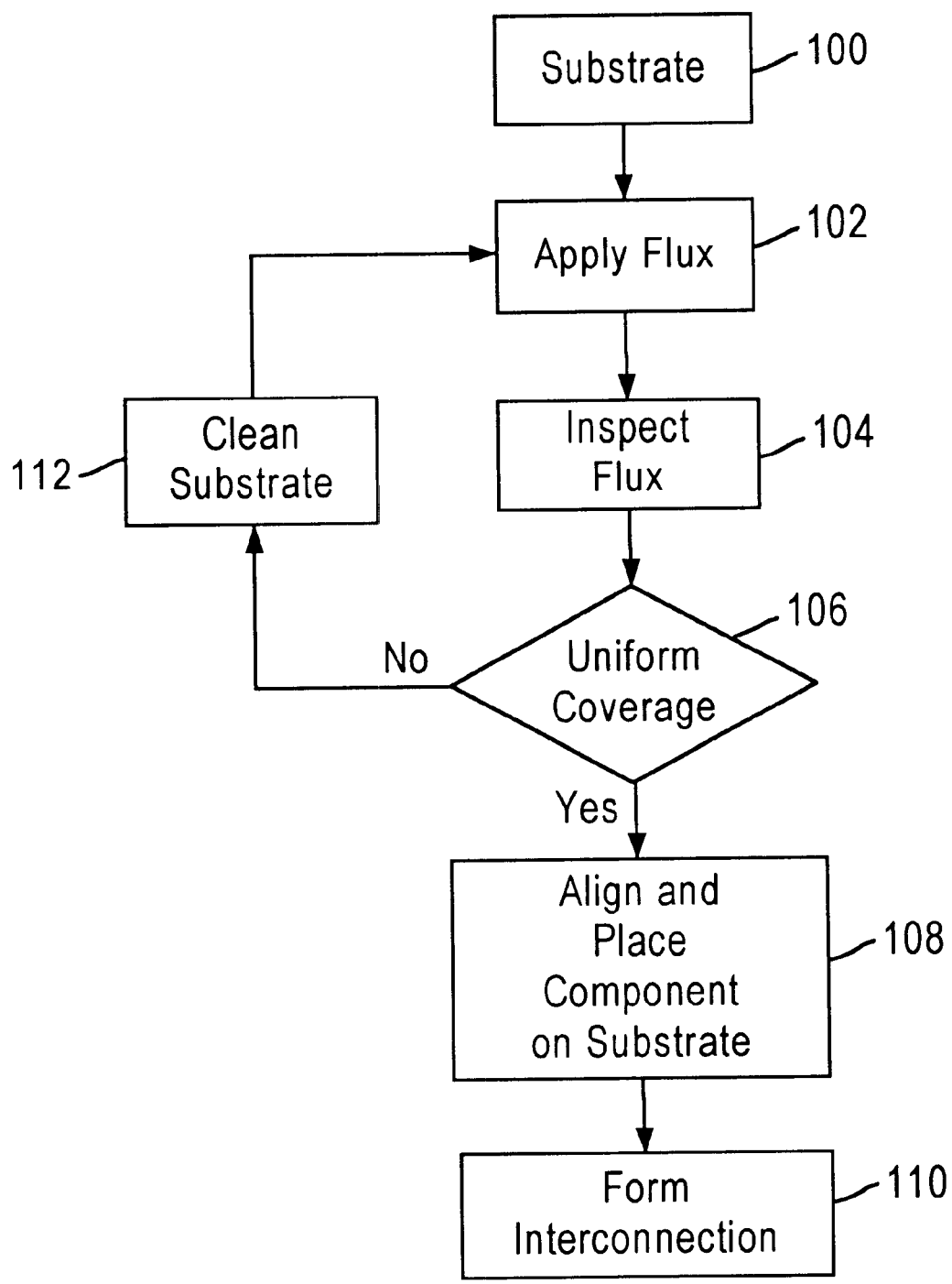
FIG. 1 shows a flow chart of packaging a device in accordance with the present invention.

The various features and advantages of the present invention will become more apparent as a detailed description of the embodiments thereof is given with reference to the appended figures. For example, a flow diagram of assembling a integrated device, e.g. a IC die, and a substrate in a flip chip configuration in accordance with the present invention is illustrated in FIG. 1. The method of the present invention begins with Step 100 by providing a substrate for mounting a device. The substrate has an array of conductive contacts corresponding to the solder bumps of the device to be mounted and joined thereto and can be made of ceramic or organic materials.

In an embodiment of the present invention, the substrate is constructed of a plurality of laminated dielectric and conductive layers, e.g. a bismaleimide-triazine (BT) resin or FR-4 board laminate, where individual IC chips are mounted to the top layer of the substrate. A pre-defined metallization pattern lies on each dielectric layer within the substrate. Metallization patterns on certain layers act as voltage reference planes and also provide power to the individual chips. Metallization patterns on other layers route signals between individual chips. Electrical connections to individual terminals of each chip and/or between separate layers are made through vias. Interconnect pins are bonded to metallic pads situated on the face of the substrate and are thereby connected to appropriate metallization patterns existing within the substrate. These interconnect pins route electrical signals between a multi-chip integrated circuit package and external devices. The array of conductive contacts on the face of the substrate can be coated with solder alloy to form bond pads or solder bumps corresponding to a particular device. Alternatively, the substrate can be fabricated from ceramic materials, such as silicon, alumina, glass, etc.

In Step 102, a thin film substrate fluxer, such as a brush or spray fluxer available from ASYMTEX is suitably charged for fluxing operations. Flux is then applied to the substrate by either brushing or spraying the flux onto the appropriate portion of the substrate. The amount of applied flux will depend on the size of the device intended to be interconnected on the substrate, the number of terminals on the device, the type of solder employed, the type of flux employed, the reflow temperature employed, the oven atmosphere, the type of substrate, etc. Flux is applied to the substrate over the areas where a solder interconnection is to be made. Such preselected areas on the substrate is generally referred to in the art as the chip pad area. The present invention advantageously enables inspection of the chip pad area for complete coverage of flux.

In accordance with the present invention, the applied flux is inspected, Step 104, to determine the coverage and/or uniformity of the applied flux in the a given chip pad area. By inspecting the applied flux, the present invention enables improved control over the formation of interconnects between the component and substrate by ensuring adequate flux coverage for the subsequent solder reflow step. The amount of flux that will be satisfactory depends on several factors, often requiring empirical determinations.

Step 106, thus, indicates a decision point as to whether the applied flux sufficiently covers the flux zone such that a reliable interconnection will be formed during reflow or whether the fluxing step needs to be repeated or the substrate disposed. When the applied flux is not adequate, the substrate is disposed or cleaned of any flux, Step 112. The substrate can be cleaned with a suitable solvent for removing the insufficiently applied flux. Such solvents include aromatics, such as xylene, toluene, terpene, etc. and alcohols, such as methanol, ethanol, isopropanol, tetrahydrofuryl-2-carbionol, etc. or mixtures thereof. After cleaning or stripping the inadequately applied flux, the substrate is ready for re-application of the flux, step 102. Suitable fluxes include rosin based fluxes, available from Alphametals of New Jersey, and no-clean fluxes, available from Indium Corporation of New York.

When the applied flux is adequate, a component, e.g. a semiconductor device, is provided for packaging, Step 108. The component can be any device having a solder terminal thereon as, for example, a IC made of at least one semiconductor material and having one of a variety of lead-based or lead-free solder bumps on the IC. The invention also contemplates the packaging of a resistor, capacitor, inductor, transistor, or any other electronic component in need of packaging and employing flux.

Step 108 further comprises contacting the component and substrate. In this process, a conventional pick and place tool is employed to retrieve a component, precisely determine the placement of the component on the sufficiently fluxed substrate and place the aligned component on in the chip pad area of the substrate. Following assembly, the device/substrate assembly is heated to reflow the solder thereby activating the applied flux and forming an electrical interconnection between the parts, Step 110.

Figure 2:
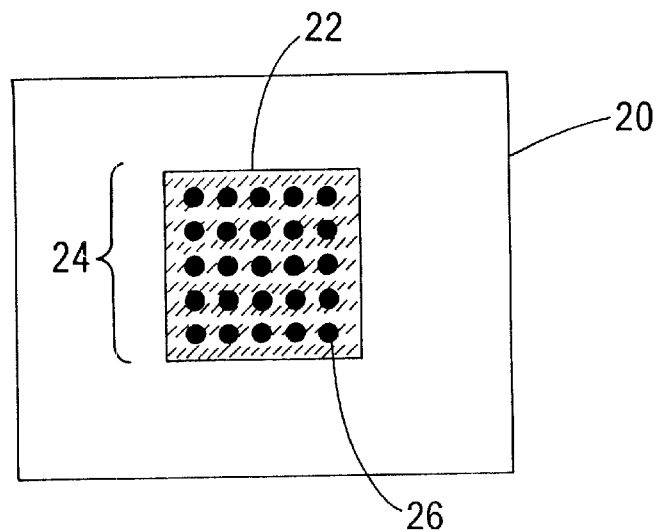
FIG. 2 illustrates a top view of a substrate having applied flux in accordance with the present invention.

In an embodiment of the present invention, the area covered by the flux will be approximately the same area occupied by an array of conductive contacts, e.g. landing pads, on the substrate. The perimeter of an array of conductive contacts can be used to define the area of the flux zone such that adequate coverage of flux is equal to the area defined by the perimeter of the array of conductive contacts on the substrate. In FIG. 2, an embodiment of the present invention is illustrated where substrate 20 has a thin film of flux 22 in chip pad area 24 over an array of solder pads 26. In an embodiment of the present invention, the applied flux approximately covers that entire area occupied by the conductive contacts.

In practicing the present invention, the applied flux is then inspected for uniformity and coverage over the flux zone area, e.g. the chip pad area. Inspecting the applied flux can comprise any optical or electro-optical method that is able to contrast the applied flux with the substrate. For example, certain fluxes are know to contain fluorescent species. The detection and quantification of specific substances by fluorescence emission spectroscopy are founded upon the proportionality between the amount of emitted light and the amount of a fluorescent substance present. Thus, when energy in the form of light, including ultra violet and visible light, is directed at the flux applied on a substrate, fluorescent substances in the flux will absorb the energy-and then emit that energy as light having a longer wavelength than the absorbed light. The emitted light from the flux can be contrasted with the substrate as determined by a photodetector or camera. In practice, the light is directed over the entire substrate at a known wavelength and the detector can be optimize to detect for the fluorescent specie in the flux composition.

In the event that a particular flux does not fluoresce or the contrast between the flux and substrate is not sufficiently defined, conventional fluorescent agents can be added to the flux composition to enhance contrast. A determination of uniformity and coverage of the flux zone containing a natural or added fluorescent agents in the flux composition can be made when the concentration of the agent is as low as several parts per million (ppm), or parts per billion (ppb), and at times as low as parts per trillion (ppt). In an embodiment of the present invention, the amount of a fluorescent specie added to the flux composition should be sufficient to provide a concentration of the specie of from about 50 ppt to about 10 ppm. The capability of measuring very low levels is an immense advantage. Such fluorescence analyses can be made in-line (i.e. during the fluxing operation), practically on an almost instant and continuous basis, with conventional equipment.

In accordance with the present invention, the uniformity and/or coverage of flux applied on a substrate comprise any optical or electro-optical method that is able to contrast the applied flux with the substrate. Separately or in addition to the fluorescent method described above, the present invention also contemplates the use of electro-optical spectroscopy, e.g. an infrared sensor or camera, to distinguish the applied flux to the substrate. The contrast between the flux and substrate can be carried out employing a conventional thermographic infrared camera. Such a camera typically uses a thermographic infrared sensor to capture an infrared image. Localized changes in temperature caused by infrared irradiation are detected by the thermographic infrared sensor. The sensor detects localized changes in temperature through changes in a value of a physical property of the sensor, such as localized changes in electrical resistance, electromotive force, or electrical charge. Should the temperature difference between the flux and substrate not be sufficient for contrast, then the fluxed substrate can be heated prior to analysis.

In an embodiment of the present, the fluxed substrate can be irradiated with heat prior to inspecting the flux with an infrared camera. Since the substrate and flux have different thermal conductivity, the absorption or release of heat can provide a sufficient temperature distribution to distinguish the flux on the substrate. A conventional infrared camera and temperature distribution-detecting means can then be employed to detect the two-dimensional temperature distribution of the flux coating and send an output signal to an imaging means, e.g. a computer.

Figure 3:
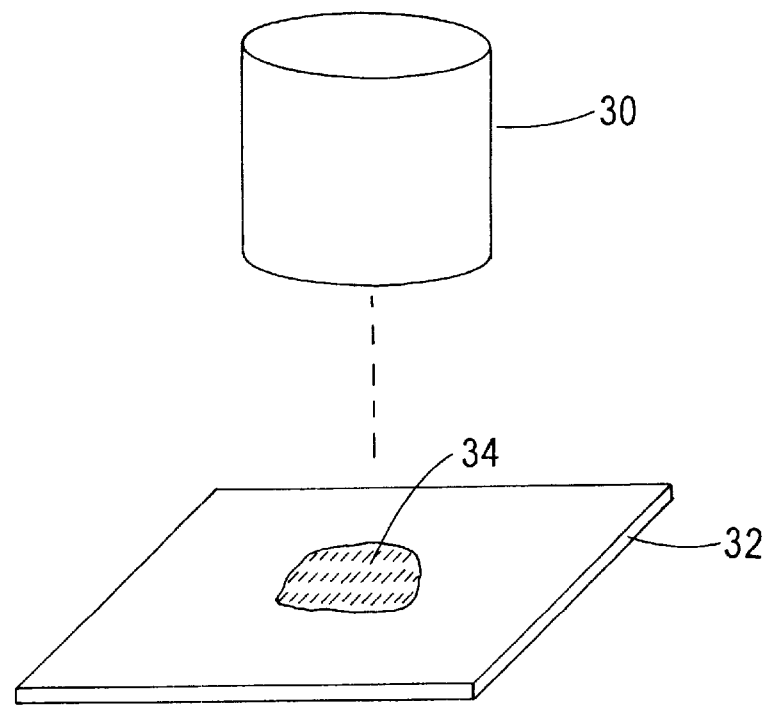
FIG. 3 shows a top view of a fluxed substrate being inspected in accordance with the present invention.

As illustrated in the embodiment of FIG. 3, an optical or electro-optical camera 30 is positioned over substrate 32 to inspect a film of applied flux 34 overlaying an array of solder pads (not shown for illustrative convenience). The present invention contemplates inspecting the applied flux to determine whether the coverage is satisfactory for a particular assembly. As discussed above, the amount of flux that will be satisfactory depends on several factors, often requiring empirical determinations. In practicing the present invention, the adequacy of applied flux can be determined by comparing the area covered by the flux to the area defined by the conductive contacts on the substrate, i.e. the flux zone or chip pad area. Thus, once satisfactory coverage has been determined for a given device/substrate assembly, the packaging process can be controlled such that when the coverage of the flux falls below or above predetermined values the process is interrupted and corrected according the steps shown in FIG. 1.

In an embodiment of the present invention, a TAC 10 flux, available from Indium Corporation, is applied over a ceramic substrate having an array of solder pads thereon for mounting a semiconductor device, e.g. such as a bumped IC die. The flux covering the area defined by the perimeter of the array of solder pads on the substrate is from about 50% to about 150% of the area, e.g. from about 100% of the area defined by the perimeter of the array of solder pads on the substrate.

When the applied flux falls within the predetermined values, the device and substrate are assembled and an electrical interconnection is formed between the device and the substrate by the application of heat. The heat can be generated by infrared radiation, a flow of dry heated gas, such as n a belt furnace, or a combination thereof, to reflow the solder and interconnect the device and substrate. In an embodiment of the present invention, the assembly is reflowed by a process of heating a laminate substrate from about 220° C. to about 270° C., by a process of a combined infrared/convection heater. When the substrate is made of a ceramic material, the electrical and mechanical interconnect between the die and substrate can be heated by reflowing the solder pads at a relatively higher temperature, such as about 350° C. to 370° C., to form the interconnections between the die and substrate to form an interconnected package.

The process steps and structures described above do not form a complete process flow for manufacturing device assemblies or the packaging of integrated semiconductor devices. The present invention can be practiced in conjunction with electronic package fabrication techniques currently used in the art, and only so much of the commonly practiced process steps are included as are necessary for an understanding of the present invention. The figures representing cross-sections of portions of electronic package fabrication are not drawn to scale, but instead are drawn to illustrate the features of the present invention.

While this invention has been described in connection with what is presently considered to be the most practical and preferred embodiments, it is to be understood that the invention is not limited to the disclosed embodiments, but, on the contrary, is intended to cover various modifications and equivalent arrangements included within the spirit and scope of the appended claims.

What is claimed is:

1. A method of inspecting applied flux on a substrate, the method comprising:

applying a soldering flux to the substrate to form a flux zone having an area approximately covering a chip pad area on the substrate, wherein the soldering flux is a rosin based composition; and inspecting the flux zone area by optical or electro-optical spectroscopy to determine the coverage and uniformity of the applied flux.

2. The method according to claim 1, comprising heating the substrate and inspecting the flux zone area by infrared spectroscopy.

3. The method according to claim 1, comprising inspecting the flux zone area by fluorescence spectroscopy.

4. The method according to claim 3, adding a fluorescent agent to the flux prior to applying the flux to enhance fluorescence of the flux.

5. The method according to claim 4, comprising illuminating the flux zone with ultraviolet or visible light after applying the flux.

6. The method according to claim 1, comprising determining the uniformity of the flux zone.

7. The method according to claim 1 comprising applying the flux to form a flux zone having the area approximately equal to a chip pad area on the substrate.

8. The method according to claim 1, comprising applying a no-clean flux on a ceramic substrate.

9. A method of manufacturing an interconnected device assembly, the method comprising:

providing a substrate having conductive contacts thereon for mounting a device, providing a device having a plurality of solder contacts thereon;

applying a soldering flux to the substrate to form a flux zone having an area approximately covering a chip pad area on the substrate;

inspecting the flux zone area by optical or electro-optical spectroscopy to determine the coverage and uniformity of the applied flux;

contacting the device and substrate such that the solder contacts of the device are aligned with the conductive contacts on the substrate to form a substrate/assembly; and forming an electrical connection between the solder contacts of the device and the conductive contacts on the substrate.

10. The according to claim 9, comprising contacting the device and substrate in response to inspecting the flux zone having adequate coverage.

11. The according to claim 9, comprising contacting the device and substrate in response to inspecting the flux zone having about 50% to about 150% of coverage.

12. The according to claim 9, comprising applying additional flux to the substrate in response to inspecting the flux zone having inadequate coverage or uniformity of flux.

13. The method according to claim 9, comprising providing a laminate substrate and reflowing the plurality of solder contacts on the device by heating the assembly from about 220° C. to about 270° C.

* * * * *

UNITED STATES PATENT AND TRADEMARK OFFICE
CERTIFICATE OF CORRECTION

PATENT NO.     : 6,597,444 B1
DATED          : July 22, 2003
INVENTOR(S)    : Jonathan D. Halderman et al.

It is certified that error appears in the above-identified patent and that said Letters Patent is hereby corrected as shown below:

<u>Title page,</u>
Item [75], Inventors, replace "San Jose" with -- Santa Clara --

<u>Column 8,</u>
Lines 11, 14 and 17, after the word "the" insert -- method --

Signed and Sealed this

Twenty-third Day of December, 2003

JAMES E. ROGAN
*Director of the United States Patent and Trademark Office*